United States Patent
Barrett et al.

(10) Patent No.: US 8,519,338 B2
(45) Date of Patent: *Aug. 27, 2013

(54) X-RAY DETECTOR INCLUDING SCINTILLATOR, A LENS ARRAY, AND AN IMAGE INTENSIFIER

(75) Inventors: Harrison H. Barrett, Tucson, AZ (US); Lars R. Furenlid, Tucson, AZ (US); H. Bradford Barber, Tucson, AZ (US); Brian W. Miller, Tucson, AZ (US)

(73) Assignee: Arizona Board of Regents on behalf of the University of Arizona, Tucson, AZ (US)

( * ) Notice: Subject to any disclaimer, the term of this patent is extended or adjusted under 35 U.S.C. 154(b) by 850 days.

This patent is subject to a terminal disclaimer.

(21) Appl. No.: 12/573,679

(22) Filed: Oct. 5, 2009

(65) Prior Publication Data

US 2010/0140487 A1   Jun. 10, 2010

Related U.S. Application Data

(63) Continuation-in-part of application No. 12/197,120, filed on Aug. 22, 2008, now Pat. No. 7,928,397.

(60) Provisional application No. 61/195,193, filed on Oct. 3, 2008, provisional application No. 60/965,910, filed on Aug. 23, 2007.

(51) Int. Cl.
*G01T 1/29* (2006.01)

(52) U.S. Cl.
USPC ............. 250/361 R; 250/370.11; 250/363.03

(58) Field of Classification Search
USPC ............................ 250/361 R, 370.09, 370.11
See application file for complete search history.

(56) References Cited

U.S. PATENT DOCUMENTS

| | | | |
|---|---|---|---|
| 3,758,780 A | 9/1973 | Lee | |
| 4,521,688 A * | 6/1985 | Yin | 250/363.04 |
| 5,245,191 A | 9/1993 | Barber et al. | |
| 5,308,986 A | 5/1994 | Walker | |
| 5,671,264 A | 9/1997 | Florent et al. | |
| 5,825,033 A | 10/1998 | Barrett et al. | |
| 6,281,509 B1 | 8/2001 | Ryan et al. | |
| 6,631,284 B2 | 10/2003 | Nutt et al. | |
| 7,129,464 B2 * | 10/2006 | Buchin | 250/214 VT |
| 7,135,686 B1 * | 11/2006 | Grady | 250/370.11 |
| 2006/0081770 A1 | 4/2006 | Buchin | |

OTHER PUBLICATIONS

Miller et al. (2006). "Single-Photon Spatial and Energy Resolution Enhancement of a Columnar CsI(Tl)/ EMCCD Gamma-Camera Using Maximum-Likelihood Estimation." Proc. SPIE vol. 6142: T1-10.*

(Continued)

*Primary Examiner* — Casey Bryant
(74) *Attorney, Agent, or Firm* — Oblon, Spivak, McClelland, Maier & Neustadt, L.L.P.

(57) ABSTRACT

An X-ray detection device including a scintillator configured to convert gamma rays or X-rays into optical radiation, an optical image intensifier configured to intensify the optical radiation to generate intensified optical radiation, an optical coupling system configured to guide the intensified optical radiation, and a solid state detector configured to detect the intensified optical radiation to generate an interaction image representing an X-ray energy emission and to perform photon counting based on data of the interaction image.

18 Claims, 4 Drawing Sheets

(56) References Cited

OTHER PUBLICATIONS

Tipnis et al. (2002). "High-Speed X-Ray Imaging Camera for Time-Resolved Diffraction Studies." IEEE Trans. Nucl. Sci. 49 (5): p. 2415-9.*

Mirzoyan et al. "A Concept for the Readout of Miltichannel Detectors by Using Analog Signal Transmission via Optical Fibres Coupled to a Fast CCD," AIP conf. Proc. (515) 358 (2000), p. 358-362.*

Nagarkar et al. "A CCD-Based Detector for SPECT," IEEE Trans. Nucl. Sci. (53) 1, Feb. 2006, p. 54-58.*

DeVree et al., "Photon Counting Gamma Camera Based on an Electron-Multiplying CCD," IEEE Trans. Nucl. Sci.(52) 3, Jun. 2005, p. 580-588.*

Gagnon, D., et al. (1996). "Maximum Likelihood Positioning in the Scintillation Camera Using Depth of Interaction." IEEE Trans. Med. Imag. (12) 1: 101-7.

De Vree, G.A., et al. (2005). "Photon-Counting Gamma Camera Based on an Electron-Multiplying CCD." IEEE Trans. Nucl. Sci. (52) 3: 580-8.

* cited by examiner

X-RAY DETECTOR INCLUDING SCINTILLATOR, A LENS ARRAY, AND AN IMAGE INTENSIFIER

CROSS REFERENCE TO RELATED PATENT DOCUMENTS

The present patent application is a Continuation-In-Part (CIP) of U.S. application Ser. No. 12/197,120, filed on Aug. 22, 2008, now being published as U.S. Patent Application Publication 2009/0050811, and claiming priority from U.S. Provisional Application Ser. No. 60/965,910, filed on Aug. 23, 2007, the present application also claiming priority from U.S. Provisional Application Ser. No. 61/195,193, filed on Oct. 3, 2008, all the contents thereof being herewith incorporated by reference.

STATEMENT REGARDING FEDERALLY SPONSORED RESEARCH OR DEVELOPMENT

This invention was made with government support under P41 EB002035 awarded by the National Institutes of Health. The government has certain rights in the invention.

BACKGROUND OF THE INVENTION (a) Field of the Invention

The present invention relates to a high-resolution, modular X-ray detector based on a scintillator plate, a lens array, and image intensifiers having a strong optical gain that are optically coupled to solid state detectors, and the use of Maximum-Likelihood Estimation (MLE) techniques to determine a position and energy of scintillation events.

(b) Brief Description of the Related Art

In the fields of digital radiography (DR) and X-ray computed tomography (CT), flat-panel scintillation detectors are used in which the scintillation light can be read out by an array of photodiodes. These detectors sense the total amount of light produced by the x-ray flux over an extended exposure period. Spatial resolution is often limited by the spread of light over from each scintillation event over multiple photodiodes and/or by the size of the photodiode elements. Scintillation detectors are also used in the related field of nuclear medicine where the goal is to image gamma rays produced by a radioactive pharmaceutical injected into a patient or animal subject.

In particular, some recent gamma-ray detectors used in Single-Photon Emission Computed Tomography (SPECT) of small animals make use of photodetector arrays in the form of CCD (charge-coupled device) cameras. In these gamma-ray detectors, a scintillation event is observed as a cluster of signal spread over multiple pixels of the CCD. A few varieties of such detectors exist and each requires the use of sophisticated low-noise, high-quantum-efficiency CCD to observe the scintillation events. Such detectors typically make use of thin scintillators optically coupled to a CCD imager where charge gain is applied within the CCD pixels. Background art CT detectors use thick scintillation plates, typically in the range of 1 mm to 2 mm, and they are physically segmented into individual pixels, typically having a cross-sectional area of 1 mm×1 mm. The physical segmentation minimizes light spread, but the resolution is strongly limited.

Another system used in small-animal single photon emission computed tomography (SPECT) utilizes a scintillator attached to an electrostatic demagnifying tube (DM) which provides slight gain and an increase in the active imaging area, but light loss in the system requires coupling to an EMCCD via a fiber-optic taper to compensate for the losses. Another CCD-based gamma-ray detector is capable of imaging individual gamma-ray interactions using an efficient optical configuration and a low-noise, high-quantum efficiency, cooled CCD camera. Substantial disadvantages of this system are that it only works with relatively thin scintillators that are less sensitive, and the CCD used for the detection must be configured to use long readout time for reduced noise which greatly reduces the frame rate capability of the system.

Moreover, background X-ray scintillation detectors respond to the total amount of light collected on each pixel during a exposure time which may be very long, around 0.1 s. This causes several problems. First, there is a randomness, called Swank noise, due to the variable amount of light, arising in large part from the random X-ray energy. Second, there is a loss of spatial resolution because the light from one X-ray photon can spread to multiple pixels. Third, X-ray photons of different energy are attenuated differently as they pass through the patient's body, leading to image defects in CT referred to as beam-hardening artifacts. Therefore, with the background art it is not possible to take advantage of the information provided by the X-ray photons for optimal diagnosis.

Despite all of the above mentioned solutions in the field of gamma-ray detection as discussed above, there is a strong need for increasing the read-out frequency of the measured scintillations in order to be able to use similar techniques in DR and CT and other applications with rapid arrival of x-ray or gamma-ray photons. Advances in systems are therefore strongly desired requiring high-speed and highly-sensitive X-ray detectors.

SUMMARY OF THE INVENTION

One aspect of the present invention provides a detection apparatus. The detection apparatus preferably includes a scintillator having a front surface and a rear surface, the scintillator configured to convert X-rays into optical radiation, and a lens array including a plurality of lens elements, the lens array arranged behind the rear surface of the scintillator, and configured to guide the optical radiation from the rear surface of the scintillator to generate a plurality of projections of optical radiation. In addition, the apparatus preferably includes a plurality of optical image intensifiers, each optical image intensifier arranged in an optical axis of a corresponding lens element of the lens array, the plurality of optical image intensifiers configured to intensify the plurality of projections of optical radiation from a rear surface of the lens array to generate a plurality of projections of intensified optical radiation, and a plurality of solid state detectors configured to detect the projections of intensified optical radiation to generate a plurality of interaction images, and configured to calculated an energy of photons of the x-rays based on the interaction images.

The summary of the invention is neither intended nor should it be construed as being representative of the full extent and scope of the present invention, which additional aspects will become more readily apparent from the detailed description, particularly when taken together with the appended drawings.

BRIEF DESCRIPTION OF THE DRAWINGS

These and other features, aspects and advantages of the present invention will become better understood with regard to the following description, appended claims and accompanying drawings where:

Herein, identical reference numerals are used, where possible, to designate identical elements that are common to the figures. The images in the drawings are simplified for illustrative purposes and are not depicted to scale.

DETAILED DESCRIPTION OF THE INVENTION

Figure 1:
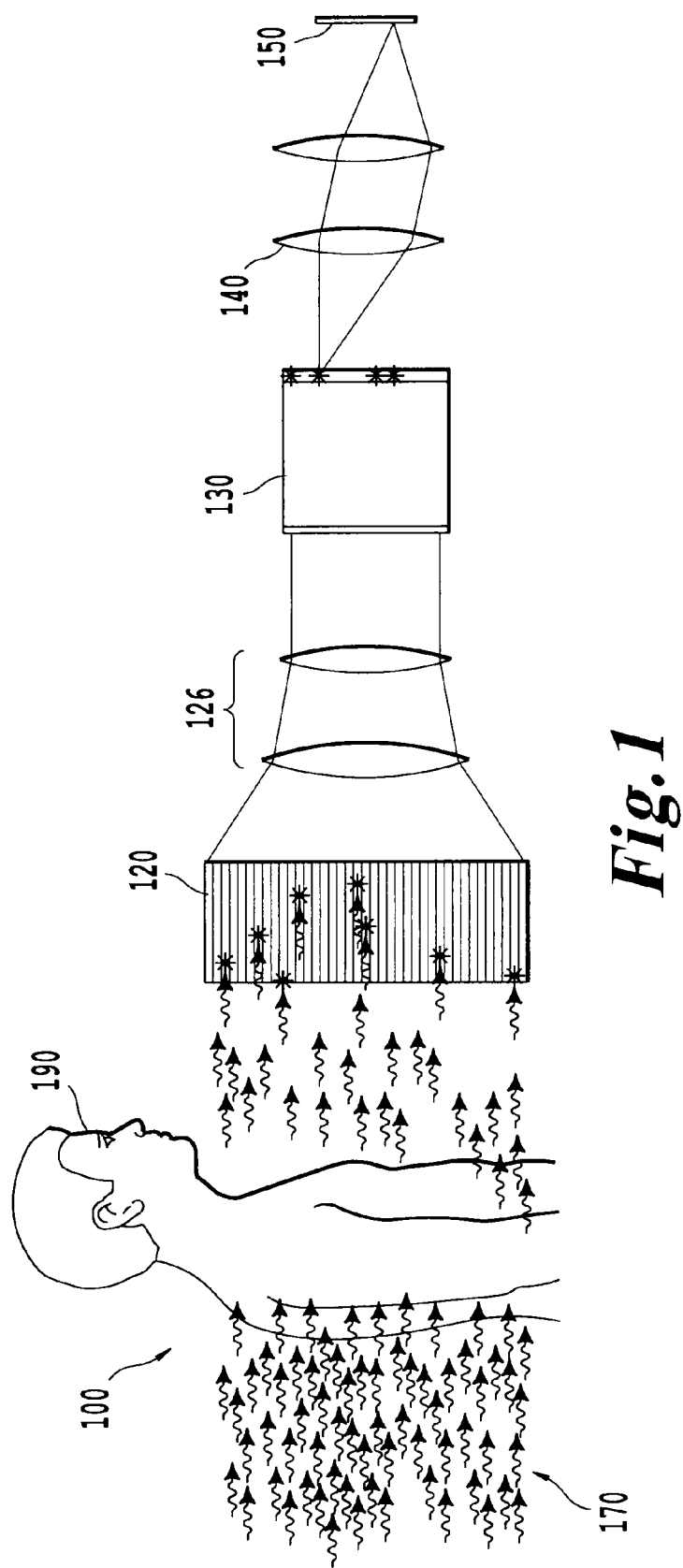
FIG. 1 shows a schematic view of the detector apparatus according to an embodiment of the present invention.

In accordance with the present invention, a X-ray detector apparatus is schematically illustrated in FIG. 1, referred to throughout by reference numeral 100. In variant, the apparatus 100 can also be configured to capture gamma rays. In apparatus 100, X-rays traverse a subject 190, for example a small animal or a human patient, and the X-rays then impinge on a scintillator plate 120. The scintillator plate 120 converts the X-rays into optical radiation that is emitted from the rear surface of plate 120. A lens system 126 can capture the optical radiation, and can project it onto an image intensifier 130. Intensified optical radiation is emitted from a rear surface of intensifier 130, and is further projected by lens 140 onto solid state detector 150, that can convert the intensified optical radiation into an image. Detector may also include hardware and software for performing data processing. The apparatus 100 is configured for X-ray photon counting, and is thereby able to measure the energy of the photon that impinges on detector 150. Lens system 126 is therefore configured to capture a very high percentage of optical photons from the optical radiation that is emitted from the plate 120.

Figure 2:
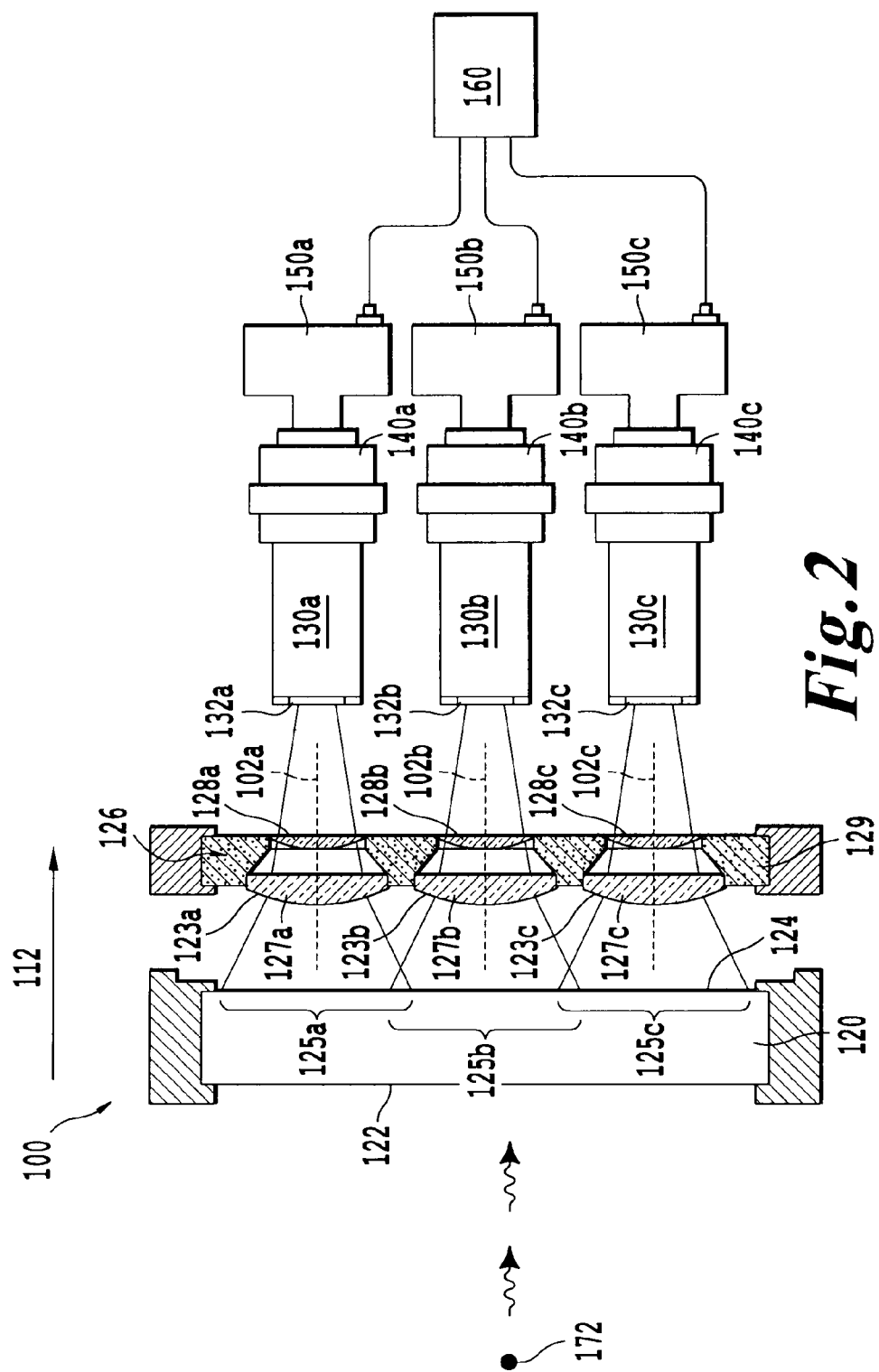
FIG. 2 shows a diagrammatical cross-sectional view of a detector apparatus having multiple detectors coupled to a single scintillator plate by using a lens array.

A more detailed view of the detector apparatus 100 is shown in FIG. 2. First, a scintillator plate 120 having a front surface 122 and a rear surface 124 is arranged, that can convert the X-rays from a corresponding source 172, for example an x-ray tube operating at 60 kVp, into optical radiation, such as visible light readable by solid state imagers, such as CCD or complementary metal-oxide-semiconductor (CMOS) image sensors. A light emitting pattern or image on a rear surface 124 of scintillator 120 is formed. In the variant shown, source 172 can be a living organism such as a mouse or human breast that was injected with a tumor-seeking radioactive tracer. In the remaining portions of the description we will refer to X-rays, but gamma rays can also be detected and processed by a correspondingly adapted detector apparatus 100, and such gamma ray detection apparatus is therefore a variant of the present invention. At a back surface 124 of the scintillator plate 122, a light-emitting pattern is generated that produces light in the visible spectrum, produced by the crystals of scintillator plate 120. The light-emitting pattern typically produces light in the wavelengths between 300 nm and 1000 nm. The scintillator plate 120 is configured to have a relatively large size, for example 15 cm×15 cm or 30 cm×30 cm. Even bigger plates for clinical purposes such as chest radiography or whole-body CT could be used.

The scintillator plate 120 can be a columnar or structured scintillator, a polycrystalline screen of the type used in X-ray detectors, or a monolithic single crystal. The scintillator can also be made of elements of segmented crystals. Many different materials can be used for manufacturing the scintillator, the non-exclusive list includes CsI(Tl), $CdWO_4$, and $Gd_2O_2S$(Tb). The scintillator absorbs the X-rays at a certain interaction depth. A scintillation event has a duration of about 10 ns to 10 µs, depending on plate 120 used. In case X-rays of higher energies have to be detected, the thickness of the scintillator plate 120 in a propagation direction 112 is chosen relatively thick. For example, the CsI(Tl) columnar scintillators preferably have a thickness between 50 µm and 1 mm, depending on the X-ray energy. With such plate thicknesses, gamma-ray energies of up to several hundred keV can be detected. More preferably, for such columnar scintillator the thickness is in a range between 50 µm and 100 µm for the 20-30 keV photons used in digital mammography. If $Gd_2O_2S$ scintillators are used for chest radiography, they preferably have a thickness between 200 µm and 500 µm. Other types of scintillators can also be used that can convert rays of a photon energy of a range of 20 keV to 1 MeV into optical radiation, such as visible light. Further improvements in scintillator material technology and manufacturing techniques will allow the production of even thicker scintillator plates 120 that could be used for detectors that could absorb even higher X-ray energies.

After the scintillator 120, a lens array 126 is arranged, having a plurality of lens elements 123a, 123b, and 123c that are held by a frame or frame 129. For purposes of clarity, only three lens elements 123a, 123b, and 123c are shown in a vertical direction, but any number of lens elements in the lens array 126 are also possible, arranged in a matrix, for example the same number of lens elements in horizontal direction, thereby having a total of nine lens elements capturing optical radiation from the rear surface 124 of scintillator plate 120. The front surface of lens array can be made the same size or larger than the rear surface 124 of plate 120. The lens elements 123a, 123b, and 123c can be aspherical type lenses, and their respective frontal fields-of-view 125a, 125b, and 125c on the rear surface 124 of the plate 120 (FOV) can overlap each other. For example, all the FOVs 125a, 125b, and 125c shown in FIG. 1 cover a vertical strip along the entire vertical extension of the rear surface 124 of the scintillator plate 120. Analogously, since lens elements can also be arranged in horizontal direction along the rear surface 122 of plate 120, for each lens elements 123a, 123b, and 123c, due to the overlapping FOVs the entire rear surface 122 of the plate 120 can be covered by these FOVs, in both horizontal and vertical direction. This allows to capture almost all the optical radiation, in the form of photons, from the rear surface 122 of the plate 120.

In the example shown in FIG. 2, each of the lens elements 123a, 123b, and 123c is made of a corresponding frontal aspherical lens 127a, 127b, and 127c, and corresponding rear aspherical lenses 128a, 128b, and 128c that are connected together by using a frame 129 holding the lenses 127a, 127b, 127c, and 128a, 128b, and 128c at a defined position. The frontal aspherical lenses 127a, 127b, and 127c are arranged on a frontal surface of frame 129, rear aspherical lenses 128a, 128b, and 128c are arranged on a back surface of frame 129, and the optical axes 102a, 102b, and 102c of the frontal aspherical lenses 127a, 127b, and 127c, and the rear aspherical lenses 128a, 128b, and 128c are aligned such that they coincide with each other. The optical axes 102a, 102b, and 102c are arranged such that the plurality of corresponding FOVs 125a, 125b, and 125c are overlapping with adjacent ones to cover the entire rear surface 124 of plate 120. Each of lens elements 123a, 123b, and 123c splits the optical radiation in form of photons emitted from the rear surface 124 of plate 120 into a plurality of projections of optical radiation.

For each of the lens element 123a, 123b, and 123c of the lens array 126, one image intensifier 130a, 130b, and 130c, respectively, is arranged. The image intensifiers 130a, 130b, and 130c are placed such that the optical axis of intensifiers 130a, 130b, and 130c and the optical axes 102a, 102b, and 102c of the corresponding lens elements 123a, 123b, and 123c coincide with each other. Again, only three intensifiers 130a, 130b, and 130c are shown in a vertical direction, but any number of intensifiers are possible, for example the same number of intensifiers arranged in horizontal direction, thereby having a total of nine intensifiers. The lens elements 123a, 123b, and 123c are configured such that the optical radiation emitted from rear surface 124 of plate 120 are projected as a plurality of projections of optical radiation onto an active front surface 132a, 132b, 132c of a corresponding image intensifier 130a, 130b, and 130c. In the example shown in FIG. 2, the rear aspherical lenses 128a, 128b, and 128c are made such that the rear field-of-view (FOV) is entirely captured by the corresponding active front surface 132a, 132b, and 132c of a corresponding image intensifier 130a, 130b, and 130c. In the variant shown, the lens elements 123a, 123b, and 123c are arranged such that there is a minification from the frontal FOV 125a, 125b, and 125c to the rear FOV projected onto surfaces 132a, 132b, 132c, for example, the lens elements 123a, 123b, and 123c can have a numerical aperture NA in the range of 0.3 to 0.8. The reduction of the size of the FOVs serves to increase the available physical space per FOV, so that the image intensifiers 130a, 130b, and 130c can be arranged in parallel and adjacent to each other.

Figure 3:
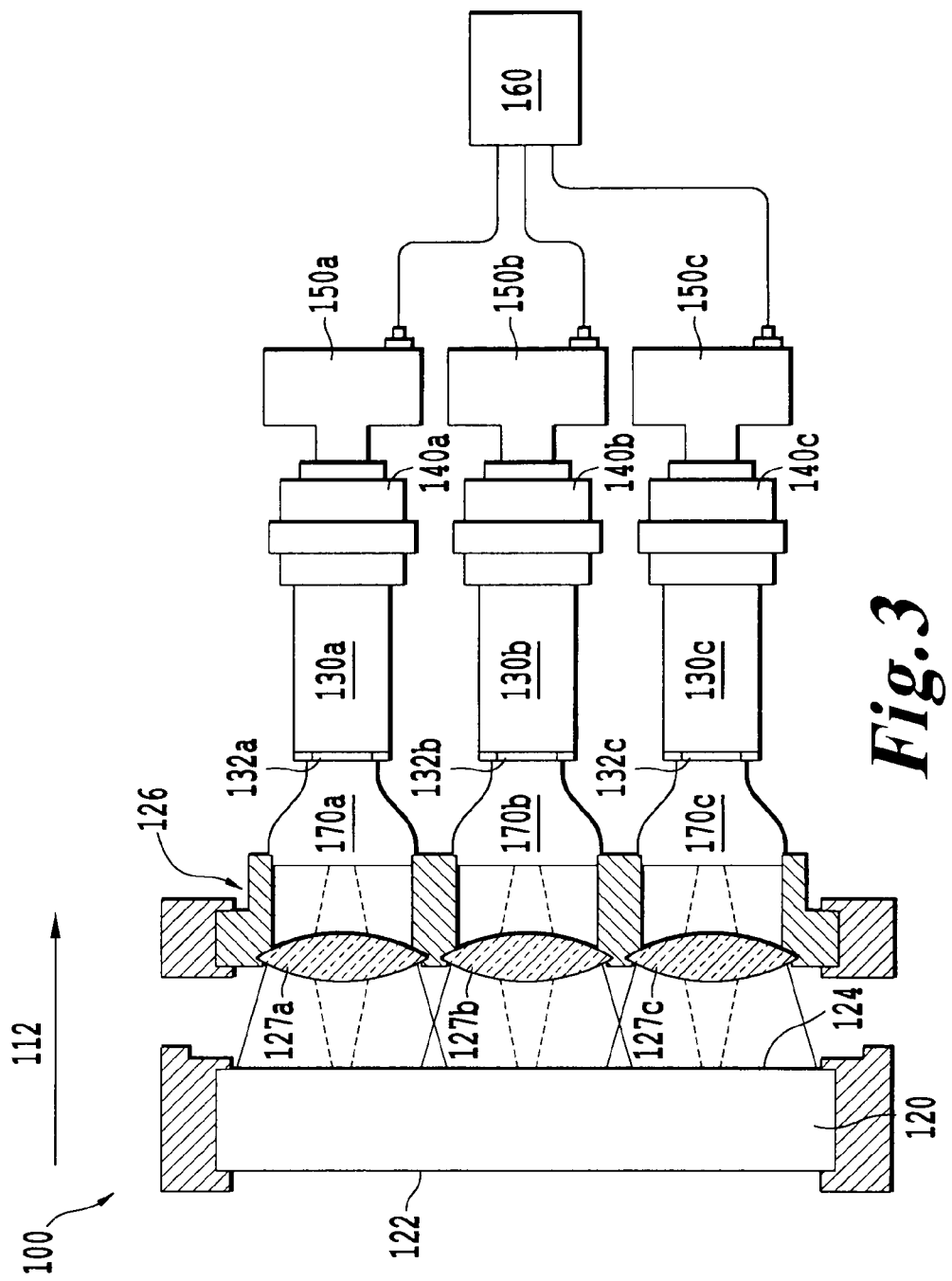
FIG. 3 shows a diagrammatical cross-sectional view of a detector apparatus according to another embodiment of the present invention having multiple detectors coupled to a single scintillator plate by using a lens array and a fiber taper.

In variant shown in FIG. 3, the lens array 126 can be made such that the front surfaces 132a, 132b, 132c of image intensifiers 130a, 130b, and 130c are in direct contact with a corresponding optical taper 170a, 170b, and 170c, that are held by frame 129. Frontal aspherical lenses 127a, 127b, and 127c are arranged such to form an image of the optical radiation onto the front surfaces of a respective taper 170a, 170b, and 170c. Holder 126 fixes lenses 127a, 127b, 127c and tapers 170a, 170b, 170c together for projection of the image on the front faces of tapers 170a, 170b, 170c. This variant provides an advantage to use image intensifiers that can be smaller in diameter and can be also less expensive. In yet another variant, as schematically represented in FIG. 10 of the parent application, it is possible to use tapers 226a, 226b, 226c that are arranged directly in contact with the rear surface 224 of scintillator plate 222, to create a large area detector. This configuration would also work for X-ray photon counting.

The projections of optical radiation produced by lens array 126 are amplified with image intensifiers 130a, 130b, and 130c by a luminous gain in a range between $10^4$ and $10^7$. It is possible that a two-stage or two-stack image intensifier is used for each intensifier 130a, 130b, and 130c, having two Micro-Channel Plates (MCPs) in series to add additional amplification. The intensifiers 130a, 130b, and 130c generate a plurality of projections of intensified optical radiation that then enters lenses 140a, 140b, and 140c that are coupled to detectors 150a, 150b, and 150c. Lenses 140a, 140b, and 140c can be made of multiple individual lenses in packed in a casing that can magnify or minify the amplified image to project a measurement image onto image sensors of detector 150a, 150b, and 150c. For example, lenses 140a, 140b, and 140c, can be macro lenses that are industrial or commercial standard lenses such as C-mount, CS-mount, F-mount, K-mount lenses, etc. with various focal lengths.

The strong optical gain from image intensifiers 130a, 130b, and 130c and the capture of many photons that are emitted from the rear surface 124 of scintillator plate 120 allow to flexibly configure the detector apparatus 100 for various applications. The optical collection of photons can be as high as 70-80% of the light that emerges from scintillator plate 120, though not all of the light from each scintillation flash event land on a single intensifier 130a, 130b, and 130c. Moreover, the photocathode of the intensifier usually has a quantum efficiency of only 10-30% for converting the collected optical photons from the optical radiation to measureable photoelectrons. The overall efficiency for converting optical photons from the scintillator to photoelectrons is around 25%. By using GaAs photocathodes for intensifiers 130a, 130b, and 130c, the overall efficiency can be up to 50%.

In other words, almost every photon of the optical radiation from plate 120 will impinge on the front surfaces 132a, 132b, 132c of the intensifiers 130a, 130b, and 130c, and therefore the optical detectors 150a, 150b, and 150c can effectively count the photons produced by an X-ray after amplification. Some losses may occur to the reflection on the front surface of lens array 126. In addition, due to overlapping FOVs of the lens elements 123a, 123b, and 123c of lens array 126, it is further ascertained that optical radiation produced by all the scintillation events on plate 120 are captured. The optical radiation caught may thereby go through several lenses before being amplified by intensifiers 130a, 130b, and 130c. The intensified optical radiation impinging on image sensors of the optical detectors 150a, 150b, and 150c is still strong enough that the noise and light loss of lenses 140a, 140b, and 140c will not substantially affect the image capturing process and the measurements on the captured image. The intensifiers 130a, 130b, and 130c suitable for apparatus 100 require very fast phosphor screens. For example PROXITRONIC Detector Systems GmbH makes 25 mm or 40 mm intensifier having 2 MCPs and having a P47 phosphor screen, that could be used for apparatus 100. P47 has a light intensity decay from 90%-10% in 100 ns and from 10%-1% in 2.9 µs.

The photon count-rate capability for a photon-counting CMOS-based sensor in detectors 150a, 150b, and 150c must be high if they are to be used in digital radiography applications. The amount of light produced by a specific photon when it interacts with scintillator plate 120 is proportional to its energy, but that energy varies randomly from photon to photon. Moreover, background X-ray scintillation detectors respond to the total amount of light collected on each pixel during a exposure time which may be very long, around 0.1 s. In this time, hundreds or even thousands of X-ray photons may generate light that ends up on a given pixel. Therefore, the count rate is limited by both the frame readout rate of the image sensors in detectors 150a, 150b, and 150c, and by the speed of data processing. The readout speed is increased by using multiple, detectors 150a, 150b, and 150c that are operated in parallel, but also by using a CMOS image sensor with ultrafast readout. This permits the recording of clusters of pixels that receive light from just a single X-ray photon interaction. The image sensors in detectors 150a, 150b, and 150c recording the energy of each X-ray photon to count individual X-ray photons at very high speed and to estimate the energy and interaction position of each photon.

Therefore the image sensor used by detectors 150a, 150b, and 150c need not necessarily be very light sensitive, and the focus can be put on high-speed image readout. Preferably high-speed CMOS image sensor are used in detectors 150a, 150b, and 150c that can have an enormous speed advantages over CCDs. In one embodiment, a Photron SA1 CMOS sensor can be used for detectors 150a, 150b, and 150c. For example, image data of the optical radiation can be captured over a region of 256×256 pixels at 67,5000 frames per second (fps). Operation at this frame rate and with a few hundred X-ray photons per frame would allow for more than $10^8$ counts per second with an acceptably small probability of overlap of some clusters. Overlap events are readily identifiable in these images, based on the shape of the cluster formed on the image, and thus may be rejected. However, it is also possible to recover many overlap events of clusters from a knowledge of single-event clusters and maximum likelihood estimation (MLE) techniques. Other types of solid state imagers such as CCD imagers photodiode-thin-film transistor image sensor, etc. can also be used, as long as they provide for high-speed image readout.

As another example, a high speed camera from the manufacturer Photron, Inc. can be used, such as the Fastcam SA5 providing up to 7,500 fps at megapixel resolution and a frame rate of 775,000 fps at a resolution of 128×24. The Fastcam SA5 has operation modes with readout rates exceeding 5 Gpixels/sec. This rate translates to full megapixel resolution at 5,000 frames/sec (fps), and over 250,000 fps at reduced resolution.

The optical detectors 150a, 150b, and 150c can include each a image processing unit, and an interface to communicate with an external processing device 160 or deliver images for visualization to an external screen. For example, raw image data or pre-processed image data that was generated by the internal processing unit of detectors 150a, 150b, and 150c can be transmitted to a personal computer or a specialized graphics computer serving as external processing device 160 for further processing, calibration, visualization, storage, and archiving. External device 160 may include a powerful graphics processor that is able to merge the partial images from optical detectors 150a, 150b, and 150c representing the optical radiation from various areas of the scintillator plate 120, to form a single image. In addition, detectors 150a, 150b, and 150c themselves can include powerful data and graphics processing functions implemented on a processor. Further processing can be applied to either the partial image captured or a single image composed from merged partial images at the external processing device 160, to detect the exact location of the scintillation events.

Tests have shown the surprising and unexpected results that by using a strong optical gain with intensifiers 130a, 130b, and 130c in detector apparatus 100, and by capturing nearly all the photons of the optical radiation that is emitted from scintillator plate 120 by use of a lens array 126 between plate 120 and a plurality of image intensifiers 130a, 130b, and 130c, system 100 is much less limited by light loss and allows great flexibility in the design of apparatus 100, and effective photon counting can be performed. In addition, the apparatus 100 can be very efficiently used in X-ray or computed tomography (CT) imaging, where the lesion detection can be improved, and the patient exposure to X-ray or doses of radioactive isotopes used for SPECT can be substantially reduced.

In addition, the detector 100 can be used for SPECT imaging, where radioactive isotopes are used and are introduced to a patient, that can label a biologically active molecule. These biologically active molecules can be in form of a tumor that can be exposed to gamma-ray radiation. The resulting tomographic images can display in three dimensions the distribution of this molecule within the patient's body. In each radioactive decay, a single gamma-ray photon can be produced, that will traverse the scintillator 120 and will be emitted therefrom as optical radiation. An advantage of apparatus 100 used with gamma-ray radiation is to substantially increase the detector area, and can thereby provide a much larger field of view or higher spatial resolution.

The information content of a medical image, such as images resulting from SPECT or CT imaging, can be quantified by how well a physician can perform a specific task, for example the detection of a subtle tumor or the estimation of a tumor's size. Background art computed tomography systems require very high radiation doses to perform this task, comparing to apparatus 100. The apparatus 100 according to the present invention allows to substantially reduce the patient dose, and can improve resolution and sensitivity of lesion detection in patients. By using high-speed image sensors as detectors 150a, 150b, and 150c, that are capable to operate at high frame rates, for example 10,000 frames per second or more. X-ray photon counting can be performed when a given image frame of data results in non-overlapping or sparse x-ray clusters on the image. Such detection by apparatus for photon-counting is only possible with the optical gain provided by image intensifiers 130a, 130b, and 130c, for example by using MCP intensifiers.

Analogously to the gamma-ray imaging that was described in the parent application with the Ser. No. 12/197,120, X-ray photon counting allows to estimate a three-dimensional position and the energy of individual X-ray interactions in the scintillator plate 120, for example by a maximum-likelihood estimation (MLE) method. A computed tomography (CT) system that is based on apparatus 100 of the present invention would provide for 10 to 100 times more information than background art CT detectors, due to the possibility of measuring the energy of each photon and determining its interaction position based on images captured by the detectors 150a, 150b, and 150c at sub-pixel resolution. This can result in an increase of the spatial resolution of a factor 10, which in turn allows the detection of much smaller lesions in patients. While image readout speed can be gained with detectors 150a, 150b, and 150c by using pixel binning, the MLE method can provide results in sub-pixel spatial resolution. Also, as explained in the parent application with the Ser. No. 12/197,120, the MLE method can localize the scintillation event on plate 120 even in the presence of blur caused by thickness of plate 120.

As discussed above, one substantial improvement is the reduction in dose radiation that has to be delivered to the patient, and this goal is mainly achieved with apparatus 100 by capturing nearly all photons with lens array 126 and strongly amplifying the optical radiation with intensifiers 130a, 130b, and 130c. Photon counting eliminates uncertainty about how many X-ray photons traversed the patient for each measurement and about the contribution of each photon to the final signal, represented in form of an image that is generated by detectors 150a, 150b, 150c. Energy information can be used to eliminate image artifacts and to optimally weight the photons in the final image of detectors 150a, 150b, and 150c for best task performance. Additionally, apparatus 100 does not suffer from inherent noise sources found in background art detectors such as read noise and Swank noise, a noise resulting from variations in light output when operating in integration mode that is typical for CCD image sensors. At the expense of a lower X-ray photon collection efficiency and a higher dose, background art integrating detectors conventionally utilize thin phosphors, in range between 50 μm to 200 μm as scintillation plates for high resolution imaging; a thick scintillator plate would produce undesirable image blur. However, in light of the substantial improvements achieved by the present invention, apparatus 100 shows the unexpected results that the combination of photon counting, for example by using high-speed CMOS image sensors, and the use of a thicker scintillator plate 120, in the range of 0.1 mm to 3.0 mm, more preferably 0.3 mm to 1.0 mm, can be used to increase x-ray absorption efficiency and thereby reduce dose, without impacting the detection resolution.

An additional aspect of the present invention is the processing of the image data obtained from detectors 150a, 150b, and 150c, such processing can be implemented as instruction code in the hardware processing unit 160, for example a personal computer connected to a plurality of detectors 150a, 150b, and 150c, a parallel supercomputing processing system, dedicated graphics processing system, etc., or the processing unit 160 can also be an integral part of detectors 150a, 150b, and 150c that communicate with each other.

Because the fields-of-view 125a, 125b, and 125c in apparatus 100 are overlapping, a scintillation event that occurs in the overlapping areas will appear on two or more different images captured by adjacent detectors, for example detectors 150a and 150b. Therefore, a special processing is required to identify clusters of pixels that were caused by the same scintillation event on rear surface 124 of plate 120. Data from all of the clusters of images from detectors 150a, 150b, and 150c must be used together in the MLE method step to get optimal performance, including an estimation of the position and the energy for each scintillation event. Assuming an ideal case were no geometrical distortions in each lens element 123a, 123b, and 123c of lens array 126 or intensifiers 130a, 130b, and 130c occur, and the capturing of images by detectors 150a, 150b, and 150c are perfectly synchronized, it would be straightforward to predict the location of a cluster on one detector and its location on an adjacent detector, because the cluster appearing on both images would be substantially the same. In practice, some form of distortion correction would be required, to efficiently and precisely calculate all the interaction positions and interaction energies.

Figure 4:
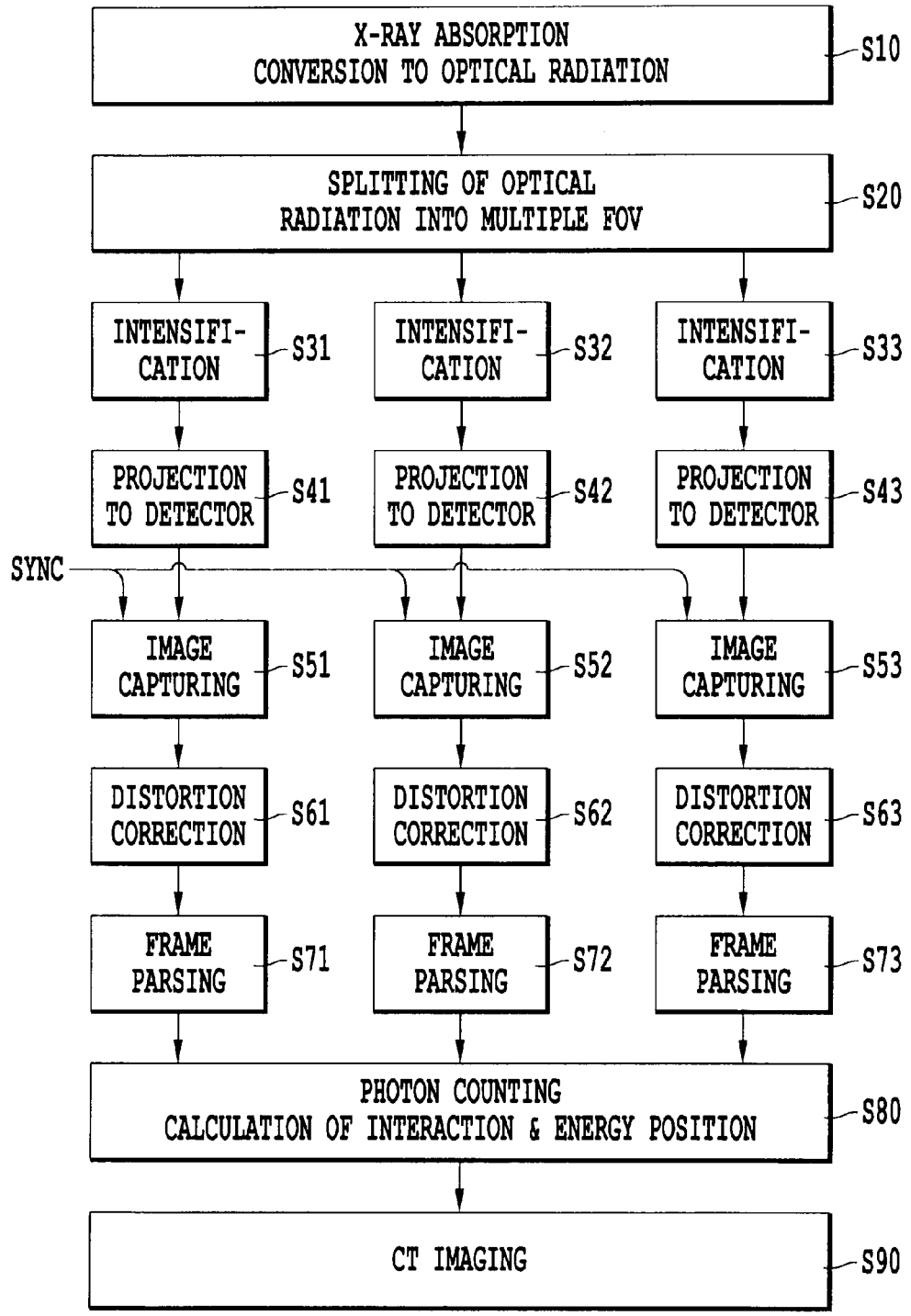
FIG. 4 shows a diagram representing the steps of a method to calculate or estimate positions and the energy of an x-ray interaction according to another aspect of the present invention.

An exemplary method for implementing the calculation of the interaction position (X, Y, and Z) and the interaction energy (E) is represented in FIG. 4. In a first step S10, an X-ray interacts in the scintillator plate 120 and produces optical radiation including at least one light emitting pattern on back surface 124 of plate 120. Next, in step S20, the entire optical radiation from the area of the back surface 124 of scintillator plate 120 is projected onto different front surfaces 132a, 132b, and 132c of intensifiers 130a, 130b, and 130c by use of a lens array 126, generating projections of optical radiation. In a case the light emitting pattern on surface 124 is located in an intersection of two different fields-of-view of 125a, 125b, and 125c different lens elements 123a, 123b, and 123c of the lens array 126, very similar clusters of the same scintillation event will be produced. These clusters are not in fact duplicates, because they are statistically independent and therefore convey independent useful information about the same event, and also because they are affected differently by optical aberrations. Next, for each lens elements 123a, 123b, and 123c of the lens array 126, the projections of optical radiation are amplified with intensifiers 130a, 130b, and 130c. For purposes of simplification and clarity, the method shown in FIG. 4 only shows three steps S31, S32, and S33 of intensification or amplification, symbolizing the vertically arranged intensifiers 130a, 130b, and 130c. However, depending on a total number of vertically and horizontally arranged lens elements 123a, 123b, and 123c of lens array 126, and corresponding intensifiers 130a, 130b, and 130c in a matrix behind scintillation plate 120, more such steps S31, S32, and S33 can be performed in parallel. This rationale of additional parallel steps is also applicable regarding the remaining steps that are performed in parallel.

After the projections of optical radiation, including at least one light emitting pattern, are amplified or intensified by intensifiers 130a, 130b, and 130c, the projections of intensified optical radiation are focused onto detectors 150a, 150b, and 150c by the use of lenses 140a, 140b, and 140c, each of these lenses associated to one detector, in step S41, S42, and S43. In these steps, light exiting the intensifiers 130a, 130b, and 130c is projected to an active surface of and image sensor of detectors 150a, 150b, and 150c. Next, in steps S51, S52, and S53, the image generated by the projections of intensified optical radiation is then captured by the image sensor of detectors 150a, 150b, and 150c and converted to digital image data, forming a plurality of images. The capturing of the images by detectors 150a, 150b, and 150c is synchronized by a synchronization signal, to ascertain that the plurality of images are captured in parallel at the same time instance. In steps S61, S62, and S63, the plurality of images captured are subjected to distortion correction that was introduced by the respective optical path. These steps S61, S62, and S63 can include filtering and noise removal.

In addition, each of the plurality of images is corrected to reduce distortion, so that the plurality of images have the same geometric references. For example, intensifiers 130a, 130b, and 130c can introduce artifacts to an intensified image, such as lag, vignetting effects, pincushion distortion, and the S distortion, depending on what type of intensifiers 130a, 130b, 130c are used. The lag of an intensifier 130a, 130b, and 130c is the persistence of luminescence that acts like a low-pass filter on the light emitted from back face of intensifier 130a, 130b, and 130c, and can be expressed as a time constant. This time constant may limit the precision of the photon-counting and thereby also the calculation of the interaction position and energy, and can also limit the frame rate that is usable. It is important that intensifier 130a, 130b, 130c have a very short time constant, for example in range of 1 μs to 5 μs, so as not to limit the usable frame rate. Due to vignetting effects and radiometric effects, it is possible that the light intensity varies strongly with position in the image.

Intensifiers 130a, 130b, 130c may also cause geometric distortions such as the pincushion distortion and the S distortion. Pincushion distortion is a geometric, nonlinear magnification across the image, where a magnification difference at the periphery of an intensified image and can be caused by intensifiers 130a, 130b, and 130c and the lenses 140a, 140b, and 140c. The external processing unit 160 or an internal pre-processing hardware and/or software to detectors 150a, 150b, and 150c can be configured to store calibration data and algorithms to compensate any of the distortions introduced, for example the artifacts that are introduced by intensifiers 130a, 130b, and 130c, distortions generated by lenses 140a, 140b, and 140, and noise introduced by image sensors of detectors 150a, 150b, and 150c. The distortion correction performed on all of the plurality of images can guarantee that the images are calibrated to a common reference plane, for example a reference plane defined by the rear surface 124 of plate 120.

Thereafter, in steps S71, S72, and S73, frame parsing is performed with each of the plurality of images that were captured by distortion-corrected. The frame parsing identifies all the pixels in each cluster of pixels associated with a respective X-ray scintillation event. For example, the spatial coordinates and the amplitude of all pixels that belong to each cluster are identified. Because some of the fields-of-views 105a, 105b, and 105c are overlapping, for example fields-of-view 105a and 105c have an overlapping area, some of the clusters in two adjacent images may be the same, but located at different position in the respective image. Accordingly, all the detected clusters in all the images can be labeled with an unique identifier in steps S71, S72, and S73, can be assigned with the coordinates of their location on the respective image sensor of detector 150a, 150b, and 150c. Moreover, each cluster can also be tagged with an identifier that designates which of the respective detector 150a, 150b, or 150c captured the cluster. This metadata associated with each cluster can be used for further processing.

Next, in step S80, the pixels of the clusters found, together with the associated metadata, are processed to generate a parameter set including the position and the energy of an x-ray interaction on the plate 120. A data set in form of a vector can be generated, where a total number of elements is the number of measurements. For example, if a cluster is a 3×3 pixel region on the captured image, and only a single cluster is used for the estimation, this means 9 measurements have been performed and 9 elements would be in the data vector. In a case two such clusters are used, both having a 3×3 pixel region, 18 elements would be in vector g.

The clusters from one interaction have to be concatenated into an overall data vector g for that interaction. One X-ray interaction may produce multiple clusters especially in light of the high-speed image capturing of detectors 150a, 150b, and 150c. The vector g including the pixel data of at least one cluster that belong to a scintillation event can be subjected to an MLE algorithm, so as to precisely determine the position and the energy of an x-ray interaction. By using the information from all pixels in a cluster, or multiple clusters associated with the same interaction, it is possible to estimate the interaction position, thereby not only eliminating the blur arising from light spread but also making it possible to determine the interaction location with sub-pixel accuracy. In addition, in a case a thick scintillator is used, and X-ray photons enter it at oblique incidence, we can also estimate the depth of interaction, thereby eliminating the blur due to parallax. Thus MLE position estimation is capable of eliminating three major sources of blur, the light spread, the pixel size, and parallax. In a next step S90, further processing can be applied to the parameter set, such as calculation of visualization data with three-dimensional graphics processing, storage, analysis, data communication, etc. The external processing unit 160 can also be programmed to merge the calibrated images together, to create one single image from one parallel and synchronized image capturing event, before subjecting them to the MLE algorithm.

To speed up the frame parsing in steps S71, S72, and S73, it is possible to reduce the image data by making use the optical characteristics of plate 120, lens array 126, and intensifiers 130a, 130b, and 130c, and image sensors of detectors 150a, 150b, 150c. The resulting image resolution can thereby be reduced, without the use of digital image processing algorithms that can slow down the throughput speed of apparatus 100. For example, the physical size of a cluster on detectors 150a, 150b, and 150c can be minimized by using columnar scintillators for plate 120 with a certain resolution, and carefully focusing the lens elements of the lens array 126 on the rear surface 124. Moreover, the number of pixels in the cluster can be minimized by choosing the optical magnification and/or pixel binning directly performed at the image sensor of detectors 150a, 150b, and 150c so that the cluster fits a pre-defined region of interest (ROI), for example 3×3 pixels. With such configuration of the apparatus 100, it is estimated that well over $10^8$ clusters per second can be resolved by a single camera with an acceptably small probability of overlap.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

For example, throughout the description X-rays have been described that are interacting with scintillator plates. However, the same principles can also apply and be used for gamma rays in SPECT imaging, that are absorbed by a scintillator plate made of a suitable material, for example columnar cesium iodide (Thallium) CsI(Tl), CsI(Na), NaI(Tl), $LaBr_3(Ce)$, gadolinium oxysulfide $(Gd_2O_2S)$. In addition, many other types of devices can be used to perform amplification of optical radiation by intensifier 130a, 130b, and 130c.

The invention claimed is:

1. A detection apparatus, comprising:
a scintillator having a front surface and a rear surface, the scintillator configured to convert x-rays or gamma rays into optical radiation;
a lens array including a plurality of lens elements, the lens array arranged behind the rear surface of the scintillator, and configured to guide the optical radiation from the rear surface of the scintillator to generate a plurality of projections of optical radiation for each absorbed x-ray or gamma ray;
a plurality of optical image intensifiers that each collect a substantial fraction of the light from each flash produced by a single gamma-ray or x-ray photon and each produce an amplified flash of light associated with the projections of optical radiation, each optical image intensifier arranged in an optical axis of a corresponding lens element of the lens array, the plurality of optical image intensifiers configured to intensify the plurality of projections of optical radiation from a rear surface of the lens array to generate for the amplified flashes of light a plurality of projections of intensified optical radiation;
a plurality of solid state detectors configured to detect the projections of intensified optical radiation and generate a plurality of interaction images, the solid state detectors operating at a frame rate fast enough to allow spatial separation of most of the clusters of pixels of the projections of optical radiation that received light from different gamma-ray or x-ray interactions in the scintillator; and
a processing unit programmed with instructions, the instructions when executed identify the clusters of pixels associated with respective amplified flashes of individual gamma-ray or x-ray photons and use the data from said cluster of pixels to perform a statistical estimation of a position where the corresponding gamma-ray or x-ray photon interacted with the scintillator and the energy deposited in the interaction.

2. The detection apparatus according to claim 1,
wherein the plurality of projections of optical radiation are captured by the lens array from a plurality of corresponding area sections of the rear surface of the scintillator, and
wherein the plurality of the lens elements of the lens array have overlapping fields of view, such that adjacent area sections of the rear surface are overlapping each other.

3. The detection apparatus according to claim 1, further comprising:
a plurality of lenses configured to project the plurality of projections of intensified optical radiation onto the plurality of solid state detectors, respectively.

4. The detection apparatus according to claim 1, wherein a surface of the lens array has at least a same total area as the rear surface of the scintillator.

5. The detection apparatus according to claim 1, wherein said processing unit is configured to:
produce from said data an interaction image;
subtract a background image from the interaction image;
identify pixels of the interaction image that are above a certain threshold intensity value within a region-of-interest to define a cluster;
calculate a centroid of the cluster; and
generate a mean value of all the pixel that are located within the region-of-interest.

6. The detection apparatus according to claim 5, wherein said processing unit is configured to:
use a maximum-likelihood algorithm to estimate a vertical position, a horizontal position, said energy, and a depth of interaction of the x-rays in the scintillator.

7. The detection apparatus according to claim 6, wherein said processing unit is configured to:
calculate a kurtosis value for the cluster of pixels.

8. The detection apparatus according to claim 1, wherein optical radiation of each amplified flash has a wavelength in a range from 100 nm to 1000 nm.

9. The detection apparatus according to claim 1, wherein the scintillator comprises at least one of a columnar scintillator, a scintillation screen, or a monolithic scintillator.

10. The detection apparatus according to claim 1, wherein at least one of the optical image intensifiers comprises:
a photocathode made of at least one of Bialkali Antimonide, Multialkali Antimonide, Gallium-Arsenic-Phosphorus (GaAsP), or Gallium Arsenic (GaAs).

11. The detection apparatus according to claim 1, wherein at least one of the optical image intensifiers comprises a microchannel plate.

12. The detection apparatus according to claim 1, wherein a rear surface of the scintillator and a faceplate of at least one of the image intensifier are in direct contact with each other.

13. The detection apparatus according to claim 1, wherein the plurality of the lens elements of the lens array have overlapping fields of view, such that adjacent area sections of the rear surface overlap each other.

14. The detection apparatus according to claim 13, further comprising a processing unit programmed with instructions, the instructions when executed correct for distortion of images in the overlapping fields of view.

15. The detection apparatus according to claim 1, wherein the plurality of solid state detectors comprise synchronized detectors to ascertain that the plurality of interaction images are captured in parallel at the same time.

16. The detection apparatus according to claim 1, wherein the plurality of optical image intensifiers have time constants in a range of 1 μs to 5 μs.

17. An x-ray imaging system for examining an object, comprising:
an x-ray source for emission of x-rays through the object;
a scintillator having a front surface and a rear surface, the scintillator configured to convert the x-rays into optical radiation;
a lens array including a plurality of lens elements, the lens array arranged behind the rear surface of the scintillator, and configured to guide the optical radiation from the rear surface of the scintillator to generate a plurality of projections of optical radiation for each absorbed x-ray;
a plurality of optical image intensifiers that each collect a substantial fraction of the light from each flash produced by a single x-ray photon and each produce an amplified flash of light associated with the projections of optical radiation, each optical image intensifier arranged in an optical axis of a corresponding lens element of the lens array, the plurality of optical image intensifiers configured to intensify the plurality of projections of optical radiation from a rear surface of the lens array to generate a plurality of projections of intensified optical radiation;
a plurality of solid state detectors configured to detect the projections of intensified optical radiation, the solid state detectors operating at a frame rate fast enough to allow spatial separation of most of the clusters of pixels of the projections of optical radiation that received light from different x-ray interactions in the scintillator;
a processing unit programmed with instructions, the instructions when executed identify the clusters of pixels associated with respective amplified flashes of individual x-ray photons and use the data from said cluster of pixels to perform a statistical estimation of a position where the corresponding x-ray photon interacted with the scintillator and the energy deposited in the interaction; and
a processor to concatenate the plurality of interaction images into an image of the object.

18. A radiation detection apparatus, comprising:
a scintillator having a front surface and a rear surface, the scintillator configured to convert x-rays or gamma rays into optical radiation;
a lens array arranged behind the rear surface of the scintillator, and configured to guide the optical radiation from the rear surface of the scintillator to generate a plurality of projections of optical radiation for each absorbed x-ray or gamma ray;
at least one or more optical image intensifiers that each collect a substantial fraction of the light from each flash produced by a single gamma-ray or x-ray photon and each produce an amplified flash of light associated with the projections of optical radiation, each optical image intensifier arranged in an optical axis of a corresponding lens element of the lens array, the at least one or more optical image intensifiers configured to intensify the plurality of projections of optical radiation from a rear surface of the lens array to generate for the amplified flashes of light a plurality of projections of intensified optical radiation;
at least one or more solid state detectors configured to detect the projections of intensified optical radiation, the at least one or more solid state detectors operating at a frame rate fast enough to allow spatial separation of most of the clusters of pixels of the projections of optical radiation that received light from different gamma-ray or x-ray interactions in the scintillator; and
a processing unit programmed with instructions, the instructions when executed identify the clusters of pixels associated with respective amplified flashes of individual gamma-ray or x-ray photons and use the data from said cluster of pixels to perform a statistical estimation of a position where the corresponding gamma-ray or x-ray photon interacted with the scintillator and the energy deposited in the interaction.

* * * * *